(12) United States Patent
Parton et al.

(10) Patent No.: US 8,282,930 B2
(45) Date of Patent: Oct. 9, 2012

(54) MOLECULAR DELIVERY VEHICLE

(75) Inventors: Robert Glenn Parton, Ashgrove (AU); Piers Jamie Waiser, Worle (GB)

(73) Assignee: The University of Queensland, St. Lucia, Queensland (AU)

( * ) Notice: Subject to any disclaimer, the term of this patent is extended or adjusted under 35 U.S.C. 154(b) by 232 days.

(21) Appl. No.: 12/679,519

(22) PCT Filed: Sep. 24, 2008

(86) PCT No.: PCT/AU2008/001416
§ 371 (c)(1),
(2), (4) Date: Jul. 1, 2010

(87) PCT Pub. No.: WO2009/039567
PCT Pub. Date: Apr. 2, 2009

(65) Prior Publication Data
US 2010/0267846 A1    Oct. 21, 2010

Related U.S. Application Data

(60) Provisional application No. 60/974,658, filed on Sep. 24, 2007.

(51) Int. Cl.
*A61K 39/00*    (2006.01)
*A61K 45/00*    (2006.01)
*C07K 1/00*     (2006.01)
*C12P 21/06*    (2006.01)

(52) U.S. Cl. ............... 424/184.1; 424/283.1; 435/69.1; 530/350

(58) Field of Classification Search .......... None
See application file for complete search history.

(56) References Cited

U.S. PATENT DOCUMENTS

2007/0160658 A1    7/2007    Connor et al.

FOREIGN PATENT DOCUMENTS

| EP | 0848614 B1 | 4/2006 |
|----|------------|--------|
| WO | 2003/016522 A2 | 2/2003 |
| WO | 2003/087323 A2 | 10/2003 |
| WO | 2005/079854 A1 | 9/2005 |
| WO | 2007/112107 A2 | 10/2007 |

OTHER PUBLICATIONS

Murata, Masayuke, et al., "VIP21/caveolin is a cholesterol-binding protein," Proc. Natl. Acad. Sci. USA, Oct. 1995, vol. 92, pp. 10339-10343.

Ortegren, Unn, et al., "Lipids and glycosphingolipids in caveolae and surrounding plasma membrane of primary rat adipocytes," Eur J Biochem. May 2004;271(10):2028-2036.

Wolf, Anne, et al., "Ganglioside structure dictates signal transduction by cholera toxin and association with caveolae-like membrane domains in polarized epithelia," J. Cell Biol. May 18, 1998;141(4):917-927.

Li, Shengwen, et al., "Baculovirus-based expression of mammalian caveolin in Sf21 insect cells. A model system for the biochemical and morphological study of caveolae biogenesis," J. Biol. Chem. Nov. 8, 1996;271(45):28647-28654.

*Primary Examiner* — Albert Navarro
(74) *Attorney, Agent, or Firm* — Gregory P. Einhorn; Gavrilovich, Dodd & Lindsey LLP

(57) ABSTRACT

An isolated caveolin containing vesicle comprising a caveolin protein and at least one lipid, wherein at least about 30% of the at least one lipid is selected from phosphatidylethanolamine and phosphatidylglycerol is disclosed. Also disclosed is a method of making an isolated caveolin containing vesicle, an isolated caveolin containing vesicle comprising a recombinant caveolin protein, an isolated caveolin containing delivery vesicle, a method of making an isolated caveolin containing delivery vesicle and a method of treatment of a disease or condition by delivery of a molecule using the isolated caveolin containing delivery vesicle.

46 Claims, 8 Drawing Sheets

Group 1: 3 hours post-injection

Group 2: 12 hours post-injection

Group 3: 24 hours post-injection

Group 4: 48 hours post-injection

MOLECULAR DELIVERY VEHICLE

This application is a national phase patent utility filing under 35 USC §371, for international application no. PCT/AU2008/001416, filed on Sep. 24, 2008, which claims the benefit of priority to United States utility provisional patent application Ser. No. 60/974,658, filed Sep. 24, 2007. The aforementioned applications are explicitly incorporated herein by reference in their entirety and for all purposes.

FIELD OF THE INVENTION

This invention relates to caveolin-containing vesicles. In particular, the present invention relates to caveolin containing vesicles and a method of delivering molecules using these vesicles.

BACKGROUND TO THE INVENTION

Many attempts have been made to use various lipidic carriers to serve as a vehicle to transport molecules of interest.

For example EP 0848614 describes isolation and purification of endogenous microdomains or components of the mammalian cell membrane, including caveolae, and the potential use of these purified microdomains to deliver molecules, such as drugs, into various cells.

Another approach described in patent application PCT/IB2005/000204 describes bacterially derived minicells that are achromosomal products of *E. coli* or other bacterial cells, as a result of asymmetric cell division, that have intact cell walls. PCT/IB2005/000204 also describes the use of these minicells for delivery of drug molecules. The delivery may be targeted through the use of a bispecific ligand that has specificity for both the minicell surface structure and a cell surface receptor.

Li et al. (JBC, 1996, 271:45; 28647-54) describe expression of mammalian caveolin protein in insect cells and their assembly into caveolin-sized vesicles. However, these authors also describe how bacterial expression of caveolin protein fails to drive the formation of any morphological structures that resemble caveolae.

Murata and coworkers (PNAS, 1995, 92; 10339-43) describe the reconstitution of bacterially expressed caveolin into liposomes in a manner dependent upon at least one mole of exogenous cholesterol per mole of protein.

None of the above described systems permit reliable production, isolation and/or purification of a lipidic carrier with defined or consistent components. This may be due to the large degree of heterogeneity in eukaryotic vesicles.

SUMMARY OF THE INVENTION

The present invention is broadly directed to caveolin-containing vesicles comprising a caveolin protein and a lipid and/or phospholipid. Typically, although not exclusively, caveolin containing vesicles are produced in a prokaryote.

A particularly preferred form of the invention relates to an isolated caveolin containing vesicle that comprises caveolin protein and at least one lipid selected from phosphatidylethanolamine and phosphatidylglycerol.

In a first aspect, the invention provides an isolated caveolin containing vesicle comprising a caveolin protein and at least one lipid, wherein at least about 30% of the at least one lipid is selected from phosphatidylethanolamine and phosphatidylglycerol.

In a second aspect the invention provides a method of making an isolated caveolin containing vesicle including the step of allowing a caveolin protein to associate with at least one lipid, wherein at least about 30% of the at least one lipid is selected from phosphatidylethanolamine and phosphatidylglycerol, to thereby make the isolated caveolin containing vesicle.

In a third aspect, the invention provides an isolated caveolin containing vesicle comprising a recombinant caveolin protein expressed in a prokaryote associated with at least one lipid; wherein the recombinant caveolin protein and the at least one lipid associate in the prokaryote.

In a fourth aspect, the invention provides a method of making an isolated caveolin containing vesicle including the steps of: expressing a recombinant caveolin protein in a prokaryote; and allowing the expressed recombinant caveolin protein to associate with at least one lipid in the prokaryote; to thereby make the isolated caveolin containing vesicle.

In a fifth aspect the invention provides an isolated caveolin containing delivery vesicle comprising: a caveolin protein; at least one lipid, wherein at least about 30% of the at least one lipid is selected from phosphatidylethanolamine and phosphatidylglycerol; and a molecule to be delivered by the vesicle.

In one embodiment of the fifth aspect, the molecule to be delivered by the vesicle may be contained within the vesicle, integrated into a vesicle membrane and/or peripherally associated with a vesicle membrane.

In a sixth aspect the invention provides a method of making an isolated caveolin containing delivery vesicle, the method including the step of allowing a caveolin protein to associate with at least one lipid and a molecule to be delivered by the vesicle, wherein at least about 30% of the at least one lipid is selected from phosphatidylethanolamine and phosphatidylglycerol, to thereby make the isolated caveolin containing delivery vesicle.

In one embodiment of the sixth aspect the caveolin protein and molecule to be delivered are co-expressed in a prokaryote.

In another embodiment of the sixth aspect a prokaryote expressing the caveolin protein is exposed to the molecule to be delivered.

In still another embodiment of the sixth aspect the caveolin protein is prokaryotically expressed and allowed to associate with the at least one lipid to form an isolated caveolin containing vesicle and the isolated caveolin containing vesicle is allowed to associate with the molecule to be delivered by the vesicle.

In a seventh aspect the invention provides a method of making an isolated caveolin containing delivery vesicle, the method including the steps of co-expressing a caveolin protein and a molecule to be delivered; and allowing the caveolin protein to associate with at least one lipid and the molecule to be delivered by the vesicle.

In one embodiment of the seventh aspect at least about 30% of the at least one lipid may be selected from phosphatidylethanolamine and phosphatidylglycerol, to thereby make the isolated caveolin containing delivery vesicle In an eighth aspect the invention provides a method of treatment of a disease or condition by delivery of a molecule using the isolated caveolin containing delivery vesicle of the sixth aspect, or made according to the seventh aspect, to thereby treat said disease or condition.

Suitably, the molecule has therapeutic activity.

In a ninth aspect the invention provides a method for delivery of a molecule using the isolated caveolin containing delivery vesicle of the sixth aspect, or made according to the seventh aspect, to thereby deliver said molecule.

In a tenth aspect the invention provides a composition comprising the isolated caveolin containing delivery vesicle of the sixth aspect, or made according to the seventh aspect, and a pharmaceutically acceptable carrier, diluent or excipient.

In one embodiment of any of the above aspects the caveolin protein is a prokaryotically expressed recombinant caveolin protein.

In one embodiment of any of the above aspects the caveolin protein is a bacterially expressed recombinant caveolin protein.

In one embodiment of the any of the above aspects at least about 50% of the at least one lipid is selected from phosphatidylethanolamine and phosphatidylglycerol.

In one embodiment of any of the above aspects at least a portion of the at least one lipid may be endogenous to, or produced by, the prokaryote.

In one embodiment of any of the above aspects the vesicle may also comprise one or more of cardiolipin (diphosphatidylglycerol), phosphatidylcholine, phosphatidylserine and/or phosphatidyl-N-methylethanolamine.

In yet another embodiment of any of the above aspects, the vesicle may also comprise one or more phoshphoglycolipid.

In one embodiment of any of the above aspects, the vesicle may further comprise a targeting molecule.

In this specification, the terms "comprise", "comprises", "comprising" or similar terms are intended to mean a non-exclusive inclusion, such that a method, system or apparatus that comprises a list of elements does not include those elements solely, but may well include other elements not listed.

BRIEF DESCRIPTION OF THE FIGURES

FIG. 3A: A—model for formation of caveolin containing vesicles in *E. coli*. Dark-coloured dots indicate caveolin, white dots indicate a membrane impermeant fluorescent dye. In this model the dye is incorporated into the caveolin containing vesicle as they form, as shown experimentally in C. B; western blotting of MBP-Cav1 and MBP-expressing *E. coli* cells shown in C. C; Uptake of dye by MBP-Cav1-expressing, but not MBP-expressing, *E. coli*.

B: The lipid composition of purified caveolin containing vesicles resembles the composition of the host membrane. Thin layer chromatographic analysis of the lipid content of affinity purified caveolin containing vesicles. Purified lipids were run as standards for identification. PC, phosphatidylcholine; PS, phosphatidylserine; PI, phosphatidylinositol; PE, phosphatidylethanolamine; cav, lipids from caveolin containing vesicles; *E. coli*, lipids extracted from control whole *E. coli* cells. PG, phosphatidylglycerol and PE poorly resolve in the solvent system used here and make up to 10% of the membrane phospholipid in *E. coli*.

FIG. 6. Examples of transmission electron microscope (TEM) analysis of affinity purified caveolin containing vesicles. a) Negatively stained with uranyl acetate (scale bar represents 200 nm) b) Individual caveolin containing vesicles by cryo-electron microscopy in the vitrified "native" state (not stained).

Figure 7:
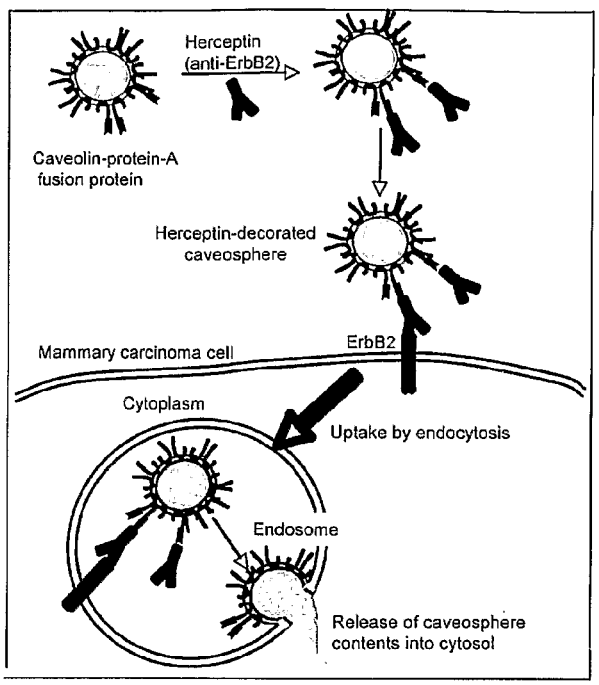

FIG. 7. Scheme for targeting of caveolin containing vesicles using a caveolin-protein A fusion protein and herceptin antibodies to ErbB2. Spheres are taken up specifically by ErbB2-positive cells into endosomes where their content is released.

Figure 8:
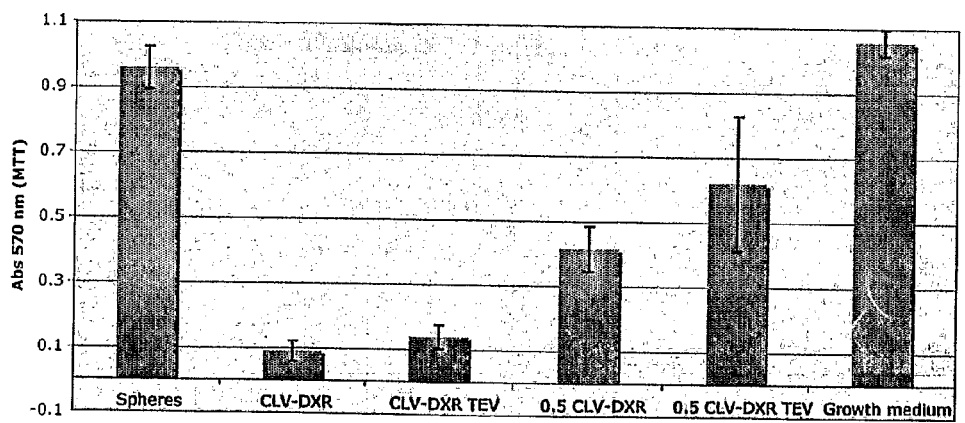

FIG. 8. Caveolin containing vesicle mediated doxorubicin toxicity. A clear dose-dependent toxicity is observed. Human mammary adenocarcinoma cells (SK-BR-3) were incubated with doxorubicin-loaded caveolin containing vesicles for 60 hours in growth medium and the effects on cell proliferation scored by MTT assay. Dosage-dependent reduction in cell proliferation is observed. The differences between non-loaded caveolin containing vesicles and growth medium addition are not statistically significant, as is the difference between the two caveolin containing vesicles preparation. (TEV=removal of affinity tag). Differences between empty caveolin containing vesicles and doxorubicin-loaded caveolin containing vesicles are significant based on single factor analysis of variance between treatments. The data represents the average of four replicates (n=4), the error represents the standard deviation. Total amounts added CLV-DXR, 22.8 µg/ml; CLV-DXR TEV, 16.2 µg/ml; 0.5 CLV-DXR, 11.4 µg/ml; 0.5 CLV-DXR TEV, 8.1 µg/ml.

Figure 9:
Figure 9:
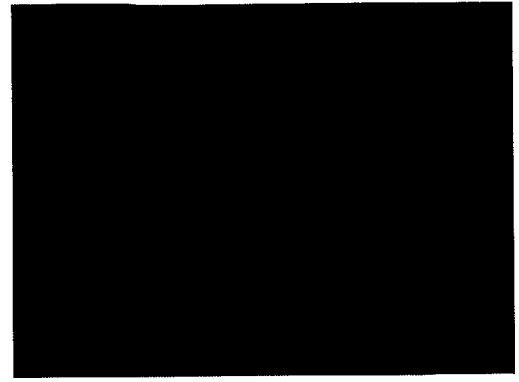
Figure 9:
Figure 9:

FIG. 9. Accumulation of Trastuzumab-loaded caveolin containing vesicles in (female) nude mice bearing an orthotopic HER2$^+$-human breast cancer tumour (BT474 derived). Fluorescein-labelled caveolin containing vesicles were conjugated with Trastuzumab/Herceptin (by means of IgG-binding to synthetic Z-domain) and injected intravenously into nude mice. The accumulation of the targeted caveolin containing vesicles in the tumour was followed over time in excised tumours and shows a clear time dependency, beginning twenty-four hours post injection.

DETAILED DESCRIPTION OF THE INVENTION

The present invention relates, at least partly, from the unexpected discovery that recombinant caveolin protein expressed in prokaryotes may associate with one more prokaryotic lipids to assemble into caveolin-containing vesicles. It will be appreciated that caveolin is not a prokaryotic protein, hence the ability of prokaryotically-expressed caveolin to associate with bacterial lipids to generate vesicles was a surprising result. Advantageously, the caveolin containing vesicles may further comprise a molecule to be delivered by the vesicle. Of significant advantage is that the caveolin containing vesicles have a relatively small size that improves efficiency of endocytosis by target cells and/or delivery thereto.

As used herein a "vesicle" is a micro-capsule comprising a vesicle wall or membrane that surrounds a lumen. Preferably, the vesicle wall is continuous and envelops the lumen.

The caveolin containing vesicle, also referred to as caveolae-like vesicles or a caveosphere, is a vesicle that comprises a caveolin protein within or associated with the lipid bilayer vesicle wall. Many molecules of caveolin protein aggregate in a quaternary or supra-molecular structure in the caveolin containing vesicle.

The caveolin protein may be any caveolin protein.

The caveolin protein may be caveolin 1, caveolin 2, caveolin 3 and/or any isoform thereof.

Preferably the caveolin protein is a mammalian caveolin protein. In one embodiment the caveolin protein is a human caveolin protein.

Preferably the caveolin containing vesicle is substantially free of endogenous bacterial membrane protein.

The caveolin containing vesicle may include one or more non-caveolin polypeptides.

The size of the caveolin containing vesicle of the invention may depend on the caveolin protein comprised in the caveolin containing vesicle.

The caveolin containing vesicle of the invention may have a diameter of less than about 250 nm. In one embodiment the diameter is less than about 100 nm. In another embodiment the diameter is about 45±30 nm, about 45±20 nm, about 45±10 nm, about 45±5 nm or about 45 nm. Preferably, the caveolin containing vesicle has a diameter of 45±5 nm. The diameter is the distance measured from membrane to membrane.

The caveolin containing vesicle of the invention may have a hydrodynamic radius less than about 300 nm. In one embodiment the hydrodynamic radius is less than about 100 nm. In another embodiment the hydrodynamic radius is about 55±30 nm, about 55±20 nm, about 55±10 nm or about 55±5 nm. Preferably, the caveolin containing vesicle has a hydrodynamic radius of 55±5 nm. The hydrodynamic radius includes the membrane and the proteinaceous coat. The hydrodynamic radius may be determined by photon correlation spectroscopy (dynamic light scattering) or any other suitable method for particle sizing. The values are the same or similar when measured by static light scattering and/or small angle X-ray scattering to determine radius of gyration.

As mentioned above this relatively small size is of advantage because it improves the efficiency of endocytosis and delivery. The small size of the caveolin containing vesicles means they are may be endocytosed by normal endocytic processes and are then broken down in the cell.

The caveolin containing vesicle also contains at least one lipid. The lipid may be a phospholipid. Preferable phospholipids include phosphatidylglycerol (PG) and/or phosphatidylethanolamine (PE). Preferably the phospholipid content of the caveolin containing vesicle includes at least about 30% phosphatidylglycerol, at least about 30% phosphatidylethanolamine and/or at least about 30% of a combination of phosphatidylglycerol and phosphatidylethanolamine. When both phosphatidylglycerol (PG) and phosphatidylethanolamine (PE) are present they may be present in different amounts.

The lipid content of the caveolin containing vesicle may include at least about 30, 35, 40, 45, 50, 55, 60, 65, 70, 75, 80, 85, 90, 91, 92, 93, 94, 95, 96, 97, 98 or 99% phosphatidylglycerol (PG) and/or phosphatidylethanolamine (PE).

The lipid content of the caveolin containing vesicle may include at least about 80, 81, 82, 83, 84, 85, 86, 87, 88, 89, 90, 91, 92, 93, 94, 95, 96, 97, 98, 99% PE. Preferably the PE content is about 80%.

The lipid content of the caveolin containing vesicle may include at least about 5, 6, 7, 8, 9, 10, 11, 12, 13, 14, 15, 16, 17, 18, 19, 20% PG. Preferably the PG content is about 10 to about 15%.

The caveolin containing vesicle may also include one or more other lipid and/or phospholipid. The one or more other lipid and/or phospholipid may be constituent lipids and/or phospholipids of the host membrane in which the caveolin is expressed. Non-limiting examples of such lipids are cardiolipin, phosphatidic acid, phosphoglycerolipids, phosphatidyl-N-methylethanolamine or phosphatidylinositol mannosides.

The caveolin containing vesicle may comprise the lipid composition of the prokaryote used for expression of the caveolin. The specific lipids and/or phospholipids comprised in the caveolin containing vesicle may be the same species as found in the prokaryote used for expression of the caveolin.

The caveolin containing vesicle may also comprise one or more phoshphoglycolipid.

The caveolin containing vesicle may have an enriched amount of long chain fatty acids compared to the endogenous host membrane. By "long chain fatty acids" is meant fatty acids with carbon chains of length greater than or equal to about 16 carbons.

Preferably, the long chain fatty acids have 18 or more carbons.

The caveolin containing vesicle may have a 2 to 8 fold increased abundance of long chain fatty acid constituents compared to the host inner membrane.

The relative abundance of one or more lipid of the at least one lipid may be increased or decreased compared to the host.

The caveolin protein of the caveolin containing vesicle may be expressed in a host prokaryote.

When the caveolin containing vesicle is prokaryotically expressed, preferably at least a portion of the at least one lipid is a lipid endogenous to the prokaryote.

Advantageously, the caveolin containing vesicle is able to be produced without the addition of exogenous lipids and/or endogenous lipids. Although the caveolin containing vesicle may be produced without the addition of exogenous lipid, one or more exogenous lipid may be added to the caveolin containing vesicle.

The caveolin containing vesicle may be expressed in a host.

While expression of the caveolin containing vesicle in a host is preferred, the caveolin containing vesicle may be made synthetically by methods known in the art.

The host may be a prokaryote, such as a bacterium or an archaea and/or a mutant or variant thereof. Suitable hosts include a Gram negative bacterium and a Gram positive bacterium.

Suitable Gram negative hosts include eubacteria, *E. coli* and strains thereof, *Pseudomonas aeruginosa, Pseudomonas* sp., and *Salmonella enterica* var *Typhimurium*. Suitable strains of *E. coli* include various K-12 derivatives and B strains.

Suitable Gram positive hosts include *Lactobacillus lactis, Bacillus sutbtilis, Lactococcus lactis, Streptomyces lividans, S. coelicolor*, and *Corynebacterium glutamicum*.

Suitable archaea include, but are not limited to, *Haloferax volcanii*.

In a preferred embodiment the host is *E. coli*.

Preferably the caveolin containing vesicle is substantially free of bacterial proteins.

By "substantially free" is meant that less than 5%, less than 4%, less than 3%, less than 2% or less than 1% of the protein content of the caveolin-containing vesicle is of bacterial origin.

While not wanting to be bound by any theory, the inventors hypothesise that bacterial membrane proteins are excluded by the curvature of the caveolin containing vesicle membrane or hydrophobic mismatch between the lipids sequestered into the caveolin-lipid domain and the host transmembrane segments.

The caveolin containing vesicle may be made by allowing a caveolin protein to associate with the at least one lipid.

When the caveolin is expressed in a prokaryote, preferably the association of the caveolin protein and the at least one lipid occurs in the prokaryote. This is of significant advantage because classical reconstitution of the vesicle is not required.

To purify the caveolin containing vesicle the cells may be lysed by any suitable method including incubation with lysozyme, sonication, French press or a combination of these. Preferably the cells are incubated with lysozyme and then sonicated.

The cellular debris may then be removed by centrifugation or other suitable means.

The caveolin containing vesicles may then be isolated from the supernatant by using any suitable purification method. Suitable purification methods include any affinity purification method, for example, affinity column purification.

The purified caveolin containing vesicle may be concentrated by any suitable means, for example, ultrafiltration.

Delivery Vesicle

One or more species of a molecule to be delivered may be incorporated into, onto or associated with the caveolin containing vesicle. The one or more species of a molecule to be delivered may be referred to as a payload.

There are numerous methods to incorporate the one or more species of molecule to be delivered into the caveolin containing vesicle. One suitable method is to co-express the one or more species of molecule to be delivered and the caveolin protein.

The one or more species of molecule to be delivered may be genetically encoded as a translational fusion with the caveolin protein.

Another suitable method is to expose bacteria expressing the caveolin protein to the molecule to be delivered by the vesicle so that the molecule to be delivered is taken up by the caveolin containing delivery vesicle.

Yet another suitable method is to express the caveolin protein in a bacteria and allow the caveolin protein to associate with the at least one lipid to form an isolated caveolin containing vesicle. Then the isolated caveolin containing vesicle is allowed to associate with the molecule to be delivered by the vesicle so that it is taken up by the caveolin containing delivery vesicle.

Preferably the caveolin containing vesicle is at least partially purified before it is allowed to associate with the molecule to be delivered.

The vesicle can releasably hold and/or store one or more species of a molecule to be delivered by the vesicle.

The one or more species of a molecule to be delivered by the vesicle may be a therapeutic molecule, a drug, a small molecule, a protein, a therapeutic protein, a transmembrane protein or a peptide.

The term "drug" includes any physiologically or pharmacologically active substance that produces a local or systemic effect. A drug may be an inorganic or organic compound and includes for example, a peptide, a protein, a nucleic acid, a small molecule. The drug may be a drug derivative for example, a salt, an acid, a base, ester or an amide.

The one or more species of a molecule to be delivered by the vesicle may be cationic or may be altered to be cationic for example when the molecule to be delivered is a protein it may be altered by adding a poly-Arginine sequence.

The one or more species of a molecule to be delivered by the vesicle may become associated with and/or tethered to the outer leaflet of the bacterial membrane during caveosphere invagination and/or formation.

The one or species of molecule to be delivered may become associated with the membrane by any suitable method. Suitable methods include, but are not limited to, lipidation, addition of membrane interacting polypeptide sequences, such as, the bacterial MinD C-terminal membrane targeting sequence, or affinity for one or more bait sequence. The one or more bait sequence may be contained as a fusion peptide with the caveolin protein. An example of a suitable bait protein is the split ubiquitin domain, wherein the N-terminal half of the ubiquitin domain is fused to the caveolin protein and the C-terminal half of the ubiquitin domain is fused to the one or more molecule to be delivered.

The molecule to be delivered by the vesicle may be inside the vesicle, contained within the vesicle and/or stored in the lumen.

The molecule to be delivered by the vesicle may be integrated into the vesicle membrane. An example of a molecule that may be integrated into the vesicle membrane is a transmembrane protein or transmembrane peptide.

The molecule to be delivered may be associated with the membrane. The association with the membrane may be a peripheral association, for example the molecule to be delivered by the vesicle may be coated on the vesicle membrane.

The caveolin containing vesicle may serve as a vehicle for delivery of a molecule. For this reason the molecule to be delivered may also be referred to as a payload.

The molecule to be delivered may be in any form such as an unchanged molecule, a molecular complex and/or a pharmacologically acceptable salt.

Targeting of the Caveolin Containing Delivery Vesicle

The caveolin containing delivery vesicle may include a targeting molecule. A targeting molecule is any molecule or combination of molecules that causes, makes possible, facilitates, assists or allows for delivery of the caveolin containing vesicle to a target site.

The targeting molecule may be incorporated into the caveolin containing delivery vesicle by being allowed to associate with the caveolin protein and/or the at least one lipid.

The targeting molecule may be an antibody or any other cognate ligand and/or receptor that can target the caveolin containing delivery to a particular cell, tissue and/or organ.

The particular cell that is targeted may be any specific type of cell such as a tumour cell or a parasite.

Preferably, the target molecule is an antibody.

Antibodies may be polyclonal or monoclonal, obtained for example by immunizing an animal with the protein of interest or a fragment thereof. Antibodies may also be recombinantly produced, as is well understood in the art.

Also contemplated are antibody fragments, particularly antigen-binding antibody fragments such as Fab, F(ab')2, Fv, scFV fragments and diabodies.

The target molecule may be a bispecific ligand, which has one region specific for a single component of the caveolin containing delivery vesicle and the another region specific for a single component of a target.

An example of a bispecific ligand is a bi-specific antibody and/or a bi-specific antibody complex.

It will be appreciated by a person of skill in the art that antibodies employed for therapeutic applications in humans should have specific properties which make these antibodies suitable for use in humans. Generally, therapeutic antibodies of non-human origin are "humanised", wherein the antibody typically comprises over 90% human sequence and the complementary determining regions of a non-human antibody. Humanised antibodies are particularly advantageous for medical applications due to the decreased likelihood of eliciting a foreign body immune reaction.

As is well understood in the art, antibodies may be conjugated with labels selected from a group including a chromogen, a catalyst, an enzyme, a fluorophore, a chemiluminescent molecule, biotin and a radioisotope.

Suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution.

Fluorophores may be selected from a group including fluorescein isothiocyanate (FITC), tetramethylrhodamine isothiocyanate (TRITC), allophycocyanin (APC), Texas Red (TR), Cy5 or R-Phycoerythrin (RPE). Examples of useful fluorophores may be found, for example, in U.S. Pat. No. 4,520,110 and U.S. Pat. No. 4,542,104 which are herein incorporated by reference.

In one particular application, the targeting molecule is genetically encoded as a translational fusion with the caveolin proteins. Examples include coding sequences for single chain variable domain antibodies (scFv), camelid nanobodies, lectins and/or another cognate ligand.

In a further application, the antibody mediated targeting is achieved by genetically encoding antibody-binding domains as translational fusions with the caveolin proteins. Examples for such mediators are microbial IgG-binding proteins, for example *Staphylococcus aureus* protein A or Streptococcal protein G.

In a particular application, two or more genetically encoded targeting sequences are expressed simultaneously. The two or more genetically encoded targeting sequences may be expressed as bi- or polycistronic messages. An example of this would be combination of different translational fusions with the caveolin proteins into a single bicistronic transcript, e.g. translational fusion of a single chain antibody with caveolin combined with a translational fusion of an IgG-binding domain with caveolin. This particular application gives rise to genetically encoded bi-specific caveolin containing vesicle if combined with a suitable antibody. This particular application is thought to be not restricted to targeting molecules, but rather applicable to any suitable translational fusion with caveolin. Examples for this include, but are not limited to fluorescent protein domains for detection and protein translocation domains or pore forming domains interacting with the targeted membrane. This particular application gives rise to multifunctional caveolin containing vesicles.

Method of Treatment

It will be appreciated that treatment methods and pharmaceutical compositions may be applicable to prophylactic or therapeutic treatment of mammals, inclusive of humans and non-human mammals such as livestock (e.g. horses, cattle and sheep), companion animals (e.g. dogs and cats), laboratory animals (e.g. mice rats and guinea pigs) and performance animals (e.g. racehorses, greyhounds and camels), although without limitation thereto.

Preferably, the pharmaceutical composition is formulated with a pharmaceutically-acceptable carrier, diluent or excipient suitable for administration.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991).

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular and transdermal administration may be employed.

The mode and site of administration may be selected depending on the location of a target cell. For example, when a target cell is internal intravenous administration may be preferred.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

The present invention is not limited to therapeutic applications. For example, in some embodiments, the present invention provides compositions and methods for the use of a caveolin containing delivery vesicle as a research tool.

For example, the caveolin containing delivery vesicle may be used to deliver a molecule to a region of interest. The molecule to be delivered may be a reagent and/or reagents or a non-reactive compound such as a dye or other visualisation agent. The region of interest may be a particular cell, cell type, tissue or organ.

So that the invention may be readily understood and put into practical effect, reference is made to the following non-limiting Examples.

EXAMPLES

Manufacture of Caveolin-Containing Vesicles

We used the T7 RNA polymerase to drive expression of a standard *E. coli* plasmid containing a T7 promoter and the caveolin cDNA (and a T7 termination sequence). The experiments were performed with mammalian caveolin-1, -2 and -3 (human, dog and mouse coding sequences) as well as with fish caveolin-1.

*E. coli* BL21 (lambda DE3) or K-12 derivative cultures were grown at 37 degrees Celsius to mid log phase and then shifted to 25 degrees Celsius upon addition of the inducer (IPTG or lactose) and then incubated for 20 hours on a shaker. The T7 RNA polymerase was induced by addition of either IPTG (isopropyl-thio-beta-galactoside) or lactose to log-phase cultures (OD at 595 nm<1.0) of the expression strain in rich medium, i.e. LB broth or terrific broth.

Various fusion proteins of caveolin protein (e.g. N—/C-terminal hexa-histidine, Glutathion-5-transferase (GST) and MBP) and the corresponding controls (expressing the partner) were also expressed to demonstrate that the caveolin protein is both required and sufficient to induce the vesiculation from the inner membrane. In addition to these large affinity tags, smaller sequences such as hexa-histidine sequences were added to the coding sequence in some cases.

Figure 1:
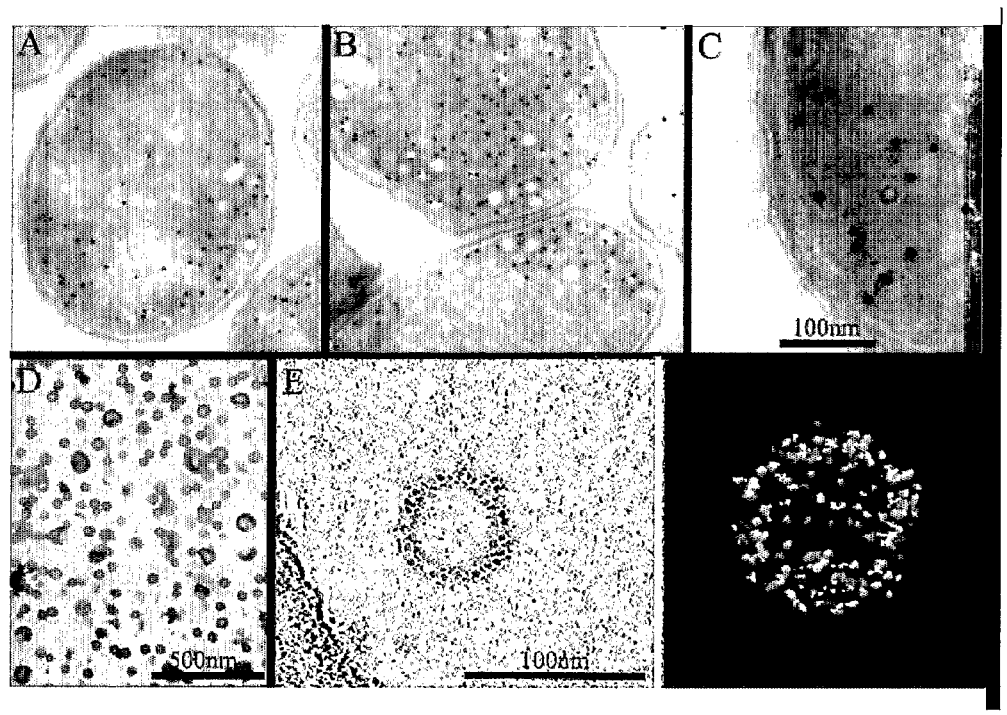
FIG. 1. Production and characterization of caveolin containing vesicles. A-C: Expression of MBP-Cav1 in *E. coli* BL21 (1DE3). After fixation, *E. coli* were processed for frozen sectioning and immunogold labelled for MBP. Expression of MBP-Cav1, but not MBP alone (not shown) induces the formation of spherical caveolin-containing vesicles-hydrodynamic radius 55±5 nm. D-E: Purified caveolin-containing vesicles were negative stained (D) or rapidly frozen (E). E: Rapidly frozen vitrified MBP-Cav1-induced caveolin-containing vesicles were viewed in the hydrated state at −160° C. and single axis electron tomograms were prepared. A single image from the tomogram is shown in which the membrane and putative individual MBP proteins are apparent (elliptoid electron dense particles). F: preliminary reconstruction of one caveolin-containing vesicle from a tomogram to show the arrangement of the MBP-caveolin fusion protein.

We then observed the formation of caveolin containing vesicles (in vivo) by electron microscopic means after thin-sectioning cells (a representative example is given in FIG. 1).

The expressed caveolin generates caveolin-containing vesicles in the eubacterial *E. coli* host. These vesicles fill the interior of the cell (FIG. 2).

The caveolin-containing vesicles can be purified to homogeneity and their structure has been analysed by negative staining and in frozen hydrated specimens after rapid freezing (FIG. 6). The caveolin-containing vesicles are spherical or substantially spherical, have a hydrodynamic radius of approximately 55±5 nm as determined by dynamic light scattering, have a homogenous size distribution and have a prominent clearly defined coat.

Figure 2:
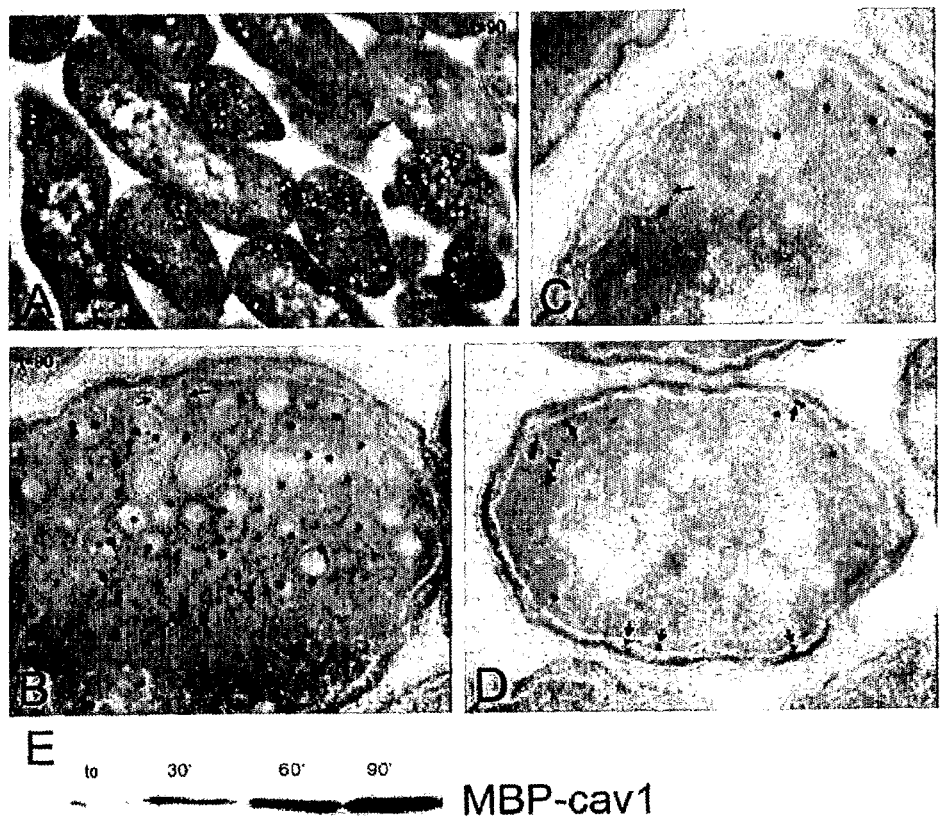
FIG. 2. Time course of expression of MBP-Caveolin-1 in *E. coli*. MBP-Caveolin-1 was induced for 90 minutes and then bacterial cultures were fixed and processed for immunoelectron microscopic localization of the MBP tag followed by 10 nm protein A gold (A, B). At low magnification it is apparent that essentially all cells accumulate MBP-positive internal vesicles. At higher magnification these vesicles have the morphology of caveolae (arrows) or budded caveolae. Examination of the uninduced culture in which there is a low constitutive level of MBP-Caveolin-1 expression (panel E) shows that MBP-Caveolin-1 is restricted to the cytoplasmic membrane of the host bacteria (arrows, panel D). Note the presence of caveola-like profiles (arrow panel C, arrowhead panel D). E; MBP-Caveolin-1 detection by western blotting at the indicated times after induction.
Figure 4:
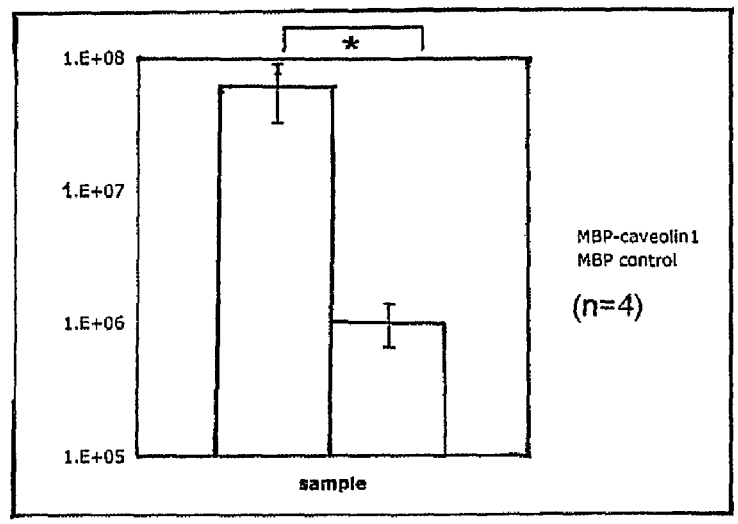
FIG. 4. Quantification of fluorescent dye uptake. Membrane impermeable fluorescent dyes were added to *E. coli* cultures during induction of caveolin containing vesicle formation (MBP-caveolin1). Cells were then washed extensively and compared with non-specific background in cells not expressing caveolin (MBP control). The upper panel shows carboxyfluorescein and the bottom panel shows tetrabromofluorescein. Statistical significance was assessed using single factor analysis of variance between treatments, * $P<0.025$, ** $P<0.001$.
Figure 4:
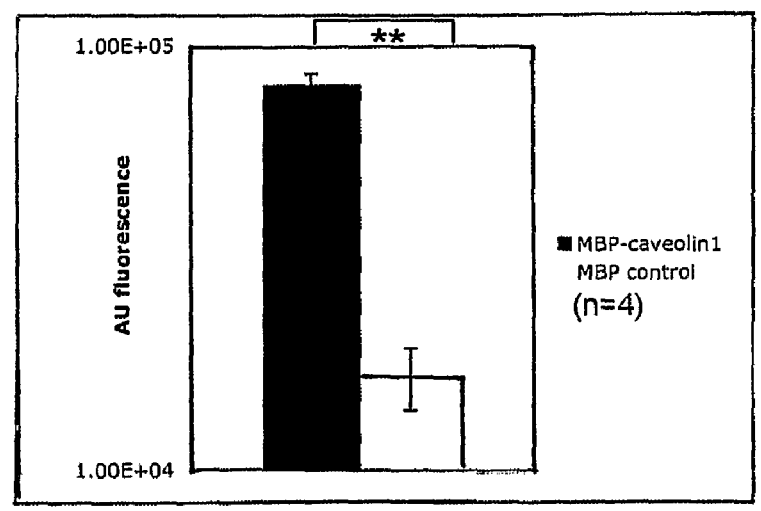

Time course immunoelectron microscopy studies suggest that caveolin-containing vesicles form as caveolin-rich domains at the cytoplasmic membrane and then pinch into the cell (FIG. 2). Consistent with this model, a dye added in the medium at the time of caveolin induction is incorporated into the caveolin-containing vesicles (FIG. 4).

The formation of caveolin-containing vesicles reflects the fundamental ability of the caveolin protein to generate caveolae in eukaryotic membranes. Key findings include:

1) as in animal cells, the caveolin protein oligomerises and integrates into the plasma membrane of the heterologous host;
2) mutants of caveolin defective in their ability to form caveolin oligomers and which do not generate caveolae in mammalian cells, do not generate caveolin-containing vesicles in *E. coli*;
3) time course experiments show that caveolin-rich domains form at the plasma membrane prior to detachment from the membrane to be released into the cytosol as caveolin-containing vesicles;
4) conformational antibodies which recognise 'mature' caveolin in caveolae at the cell surface, recognise caveolin in caveolin-containing vesicles but antibodies which recognise the 'non-mature' form of caveolin within the Golgi complex fail to do so.

Expression of Caveolin/Caveolin Containing Vesicles in Prokaryotic Expression Systems Other than *E. coli*

We have assembled an impressive array of industrially and biotechnologically relevant prokaryotic expression systems, representing impressive study of prokaryotic expression of a heterologous membrane protein. The cloning into the host has been or will be completed for the systems shown in Table 1.

Isolation and Purification of Caveolin Containing Vesicles

The caveolin containing vesicles pinch off from the cell membrane and accumulate in the cytoplasm. To purify the caveolin containing vesicles, the cells were lysed after lysozyme incubation by ultrasonic bursts (with a hand-held lab sonicator). Cellular debris was then sedimented from the lysate by centrifugation and the supernatant was applied to an affinity matrix (depending on the fusion partner, Ni-agarose, Glutathione-agarose or maltosyl-agarose). The lysate was run through the column with the affinity matrix and subsequently extensively washed in buffered saline solution. Caveolin containing vesicles were eluted from the affinity matrix in saline buffer containing the competitor for binding to the matrix, i.e. imidazole, glutathione or maltose. Caveolin containing vesicles were then concentrated to the desired degree by ultrafiltration.

For example, caveolin containing vesicles generated by maltose binding protein (MBP) caveolin-fusion protein can be purified to homogeneity on a maltose column after disrupting the *E. coli* membrane using sonication or other techniques. Electron microscopic analysis of the purified caveolin containing vesicles shows a uniform population of vesicles, mean diameter approximately 45 nm (FIG. 6).

Molecular Characterization of Caveolin Containing Vesicles

The preparations described above were used to characterise the caveolin containing vesicles in vitro by biochemical means for factors including protein composition, protein homogeneity, lipid composition and by electron microscopy, either fixed/stained with uranyl acetate or "native" in a vitrified state.

Formation

Figure 3:
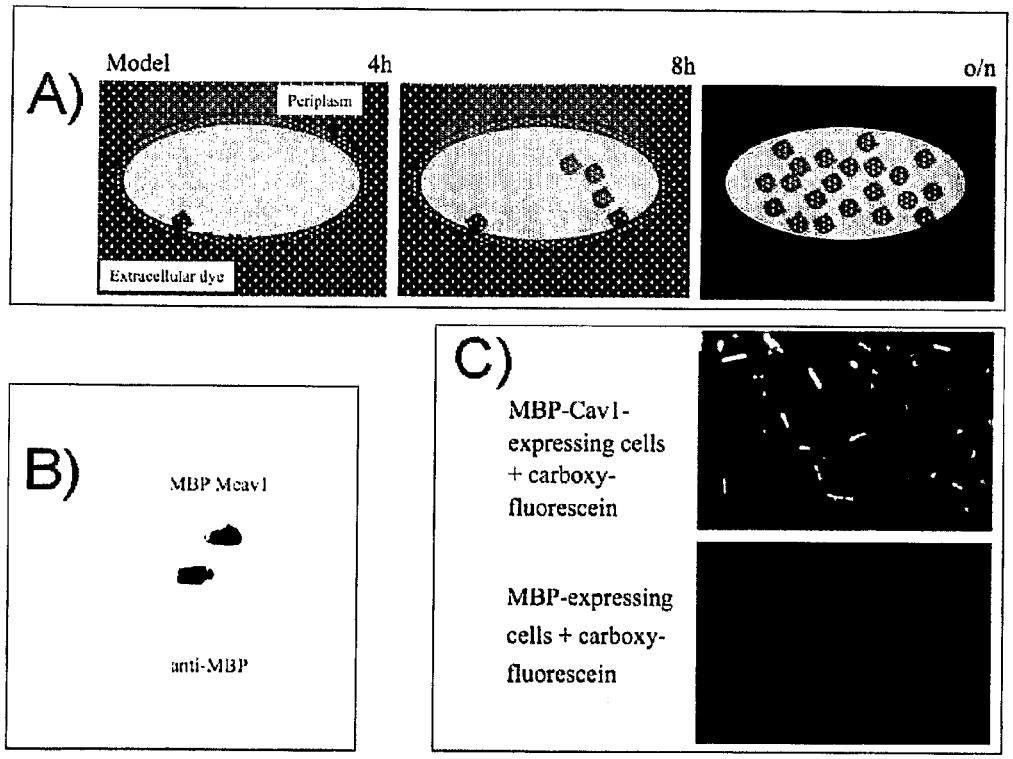
FIG. 3.

A model for formation of caveolin containing vesicles is shown in FIG. 3. Induction of maltose binding protein (MBP) caveolin-fusion protein causes rapid formation of caveolin containing vesicles from the cytoplasmic membrane of *E. coli*. The induced vesicles eventually entirely fill the eubacterial *E. coli* host (FIG. 1A to C). Time course immunoelectron microscopy studies show that caveolin containing vesicles form as caveolin-rich domains at the cytoplasmic membrane and then pinch into the cell (FIG. 2). Consistent with this model, fluorescent dyes added in the medium at the time of caveolin induction are incorporated into the caveolin containing vesicles (FIGS. 3 and 4). Control experiments have shown that this is not due to leakiness of the membrane but due to incorporation of the dye into the vesicles forming from the membrane. Caveolin containing vesicles incorporating various membrane impermeable small molecules have been purified and the contents and leakiness examined over time.

Protein Analysis

Figure 5A:
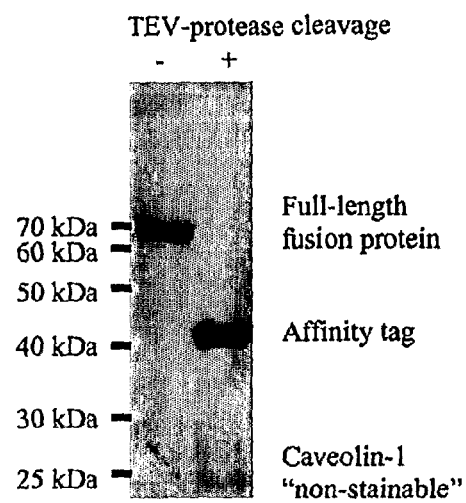
FIG. 5. A: Purified caveolin containing vesicles analyzed by SDS gel PAGE show only a single band corresponding to the MBP-Caveolin-1 fusion protein (lane 1). After cleavage of the tag using the TEV-protease the MBP is evident at approximately 40 kDa while the untagged caveolin-1 is poorly stained by the Coomassie stain (lane 2).

Standard protein analysis methods show only caveolin fusion proteins, and not other *E. coli* proteins in the purified caveolin containing vesicle preparation. That is, the caveolin containing vesicles are free or substantially free from bacterial protein. As shown in FIG. 5*a*, only recombinant protein was detected in the total protein stain. No host proteins were detected. The right hand lane of FIG. 5*a* illustrates the cleavage of the fusion protein through an engineered site.

Lipid Analysis

Figure 5B:
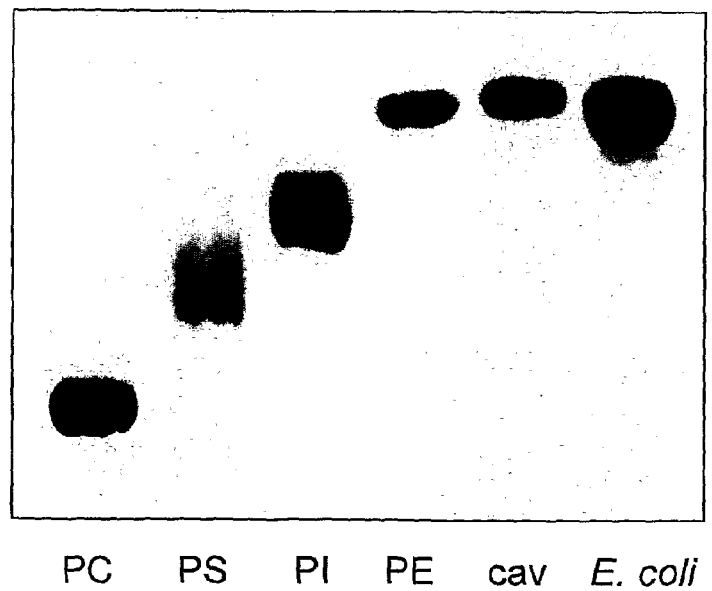

Specific lipid species are induced upon caveolin expression and integrated into the caveolin containing vesicles as determined by thin layer chromatography shown in FIG. 5*b* and by mass spectrometry which is summarized in Table 2. The main phospholipid is phosphatidylethanolamine (PE) which accounts for, an estimated, 90% or greater of the total lipids. The minor lipid components include phosphatidylglycerol (PG) and cardiolipin.

The specific lipid composition may be characteristic to caveolin containing vesicles generated in *E. coli* or other hosts and the changes induced by caveolin expression.

From PE profiling by mass spectrometry it was revealed that long chain fatty acids are enriched in the caveolin containing vesicles compared to the lipid composition of cells merely expressing the fusion partner as a control. The cells expressing the control had a higher relative content of C16 acyl chains. The augmentation of longer chain fatty acids in PE is detectable in the "whole membrane" lipid extraction as well (and to a higher level) in affinity purified caveolin containing vesicles. The stoichiometry of lipid to caveolin molecules was estimated to be approximately 70 to 1.

Further Characterisation of Structure, Stoichiometry and Composition of the Caveolin Containing Vesicles—Lipid Profiling of Caveolin Containing Vesicles The caveolin containing vesicle membrane is essentially composed of two phospholipids, phosphatidylethanolamine (PE, approximately 90%) and phosphatidylglycerol (PG, approximately 10%). Traces of cardiolipin will be present but could not be readily detected by mass spectroscopy, while traces of phosphatidic acid (PA) are present. The fatty acid composition essentially comprises three fatty acids: palmitic acid (C16:0) and the two cis-unsaturated fatty acids palmitoleic acid (C 16:1 cis-$\Delta^9$) and vaccenic acid (C18:1 cis-$\Delta^{11}$).

As shown in Table 2, whereas phospholipids with short-chain fatty acids are less frequent in caveolin containing vesicles (and indeed the whole culture expressing caveolin containing vesicles; N.B. representing the sum of cell membranes and caveolin containing vesicles membranes), fatty acids with longer chain lengths are markedly enriched. Strikingly, phosphatidic acid is considerably reduced in caveolin containing vesicle membranes. Even more surprising, dipalmitoylphosphatidylethanolamine (PE C32:0), the most abundant phospholipid in the *E. coli* membrane, is reduced in the caveolin containing vesicles compared to control membranes.

The lipid content of the caveolin containing vesicle may resemble or be influenced by that of the host. That is the component lipids of the caveolin containing vesicle may be the same species of lipid and phospholipid comprised in the host. The relative amounts of the component lipids may be the same, similar or different in the caveolin containing vesicle compared to the host.

Affinity Purification

Figure 6A:
Figure 6B:
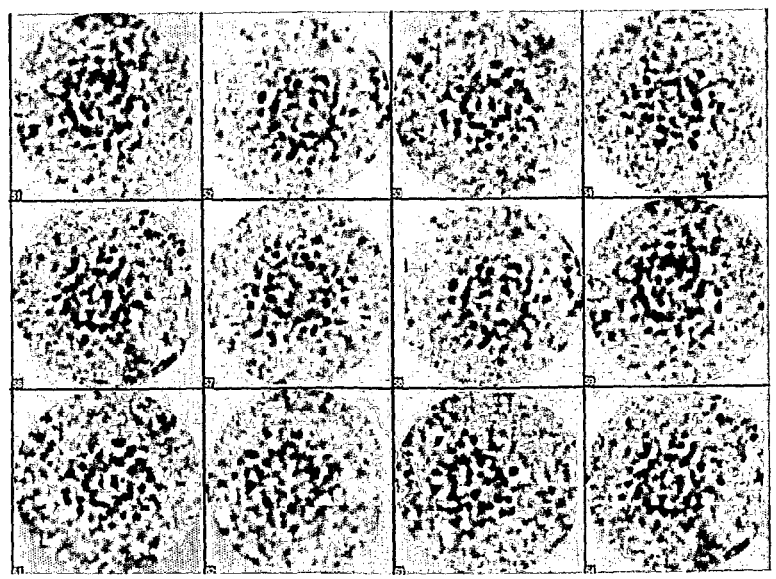

A representative example of affinity purified caveolin containing vesicles is shown in a TEM shown in FIG. 6. FIG. 6*a*) shows caveolin containing vesicles negatively stained with uranyl acetate (scale bar represents 200 nm) and FIG. 6*b*) shows individual caveolin containing vesicles by cryo-electron microscopy in the vitrified "native" state (not stained).

Electron Microscopic Analysis

Caveolin containing vesicles have been fast frozen and then analysed by high resolution EM in vitreous ice in the 300 kV cryoTEM. Cryo-EM tomography experiments show excellent structural preservation (FIG. 1E) providing information on the surface ultrastructure of the caveolin containing vesicles as seen in native vitrified specimens. Based on the characteristic shape of the MBP tag and the electron densities visible around the coat of the isolated caveolin containing vesicles, it has been estimated that approximately 160 caveolin molecules are present within one caveolin containing vesicles.

Structure of the Caveolin Containing Vesicles and Stoichiometry of Caveolin

Cryo-electron microscopic reconstruction (tomography of the sample using fourier space-weighted back-projections) of vitrified caveolin containing vesicles has allowed us to gain insight into the organisation of caveolin molecules within the caveolin containing vesicles coat. The presence of maltose binding protein (MBP), a large hydrophilic "head" on the caveolin "nail", greatly facilitates the identification of individual molecules on the surface of the sphere.

Remarkably, there are surprisingly large patches of exposed membrane present, which was predicted from our previous biochemical data. This should (and implicitly does) allow for the accommodation of additional fusion partners to the terminii of the caveolin molecules, e.g. GFP or single chain antibodies (scFv). These experiments were performed with an MBP-caveolin-GFP caveolin containing vesicles and scFv domains.

Engineering of the Caveolin Containing Vesicle Surface

Results presented herein demonstrate that it is possible to make translational fusions of caveolin with various polypeptide sequences both aminoterminally and/or carboxyteriminally that yield functional caveolin containing vesicle production. As the below list of polypeptides/proteins clearly shows, these polypeptide sequences can be of viral, prokaryotic or eukaryotic origin.

Various polypeptide sequences have been translationally fused to the caveolin coding sequences, yielding fully functional caveolin containing vesicles with the same characteristics as described above. Successfully fused polypeptide sequences includes: various affinity tags such as, maltose binding protein, glutathione-S-transferase, hexa-histidine, IgG binding domain of *Staphylococcus aureus* protein A, single chain antibody variable domains (scFv, e.g. directed to c-erb-B2 (Her2, EGF Receptor 2) or human carcinoembryonic antigen (CEA, CD66e), influenza hemagglutinin HA2, human CD8 or green fluorescent protein (GFP).

These grafted polypeptide sequences have been used to visualise caveolin containing vesicles internalisation in tumour cells (e.g. GFP) or mediate the attachment of antibodies in order to target them specifically to cells (e.g. neoplastic cells expressing HER2, as described herein). Importantly, this demonstrates that the caveolin containing vesicles can be engineered to produce a genetically encoded vesicle that may be adapted at will with targeting sequences or polypeptides that allow the conjugation with virtually any suitable antibody. This unique feature will make a large contribution to the development of personalised medicine in the near future for instance when caveolin containing vesicles with multiple specificities and/or functionalities are to be combined. The successful grafting of the influenza hemagglutinin fusion domain demonstrates that caveolin containing vesicles may be adapted to form a potentially fusogenic entity given the right environment (e.g. late endosomal pH (pH 5.5) for HA2 following receptor mediated endocytosis). This is of immense importance when delivering cargo into cells. The transfer of human CD8 (extracellular domain and transmembrane segment) onto caveolin demonstrates that transmembrane domains may be grafted onto the caveolin scaffold, which further implies that polypeptides may be included in the interior of the spheres. A preferred application would be the inclusion of therapeutic polypeptides within caveolin containing vesicles, e.g. toxins for targeted delivery to tumours or corrector peptides for the delivery into epithelial cells deficient in the transport of the cystic fibrosis transmembrane conductance regulator (CFTR).

Manufacture of Caveolin Containing Vesicles as Transport Vesicles:

In order to incorporate a molecule into the caveolin containing vesicles, a fluorescent dye, 5-(6-)carboxyfluorescein, was added about one hour prior to protein induction, i.e. in early log phase, and proceeded exactly as described above.

In the example shown in FIG. 3, 5-(6-)carboxyfluorescein was incorporated into the caveolin containing vesicle to produce a caveolin containing transport vesicle. Bacteria were co-cultured with 5-(6-) carboxyfluorescein and extensively washed. FIG. 3c) shows a micrograph of cells expressing caveolin protein and MBP expressing control cells (no fluorescence). Virtually all fluorescence is removed from the MBP expressing cultures, but remains protected within caveolin containing vesicles.

After protein expression, the cells were washed extensively by re-suspension in saline buffer and re-sedimentation. Cells expressing caveolin protein retained strong fluorescence, while control cells expressing MBP retain virtually none.

We have also washed and purified, by the methods described above, the caveolin containing transport vesicles comprising other fluorescent dyes. These solutions were subsequently strongly fluorescent. Sedimentation of these purified caveolin containing vesicles at 100,000 g RCF for 1 hour, clearly shows that the fluorescence is contained within the membranous caveolin containing vesicle, as little or no fluorescence remains in the supernatant.

Targeting and Uptake of Caveolin Containing Vesicles Caveolin Fusion Protein with IgG-Binding Domain of Protein A Targeted Specifically to ErbB2 Positive SKBr Cells and to ErbB2-Positive Colon Cancer Cells by Herceptin We have developed a targeting scheme in which information encoded in the caveolin fusion protein allows targeting of the caveolin containing vesicles using added antibodies, such as herceptin (see scheme in FIG. 7). Specific uptake of caveolin containing vesicles into early endosomes of ErbB2-positive cells using herceptin-coated caveolin containing vesicles containing a fusion protein of MBP-protein A-caveolin-GFP has been shown. No uptake of the same caveolin containing vesicles was observed when herceptin was omitted. These results validate this approach to be used in vivo.

The caveolin coding sequence was adapted with an N-terminal synthetic IgG-binding domain of S. aureus protein A (Z domain) and a C-terminal enhanced GFP. Caveolin containing vesicles were expressed and purified as described above by MBP affinity chromatography, yielding highly fluorescent caveolin containing vesicles. Subsequently, these caveolin containing vesicles were mixed with Trastuzumab (Herceptin®), a humanised monoclonal antibody against HER2 (EGF Receptor 2). HER2 expressing mammary adenocarcinoma (SK-BR-3) or human colorectal adenocarcinoma (LoVo & SW-480) were used to study the specificity of Trastuzumab-mediated targeting and uptake of the adapted caveolin containing vesicles. SK-BR-3 cells were grown in DMEM (supplemented with 20% fetal bovine serum, 1% L-glutamine) and LoVo/SW-480 in F-12 (supplemented with 10% fetal bovine serum, 1% L-glutamine). Cells were grown on glass cover slips prior to incubation with caveolin containing vesicles preparation. Caveolin containing vesicles (10~30 µg per ml) were allowed to interact with Trastuzumab (10 µg per ml) prior to incubation with the target cells in $CO_2$-independent medium. Cells were then removed from growth medium and chilled in $CO_2$-independent medium. The caveolin containing vesicles-Trastuzumab complex was added to the cells and incubated for 20 minutes while chilled. Following the incubation, cells were washed with $CO_2$-independent medium and allowed to warm up and internalise surface bound cargo, i.e. caveolin containing vesicles bound to EGFR2/HER2 by means of Trastuzumab, in regular growth medium. Cells were then acid stripped with 0.5 M glycine (pH 3.5) for 5 minutes to remove non-internalised, surface bound spheres. Incubation was continued for up to 2 hours to analyse the internalisation of the caveolin containing vesicles by means of GFP fluorescence. Cells were removed at various intervals and fixed with para-formaldehyde prior to microscopic analysis. Cancer cells that were incubated with caveolin containing vesicles+Trastuzumab, showed intense punctate fluorescence within the cytoplasm. The results of these targeting and uptake experiments clearly demonstrate that i) the caveolin containing vesicles are specifically bound to the cell surface by Trastuzumab (control spheres without the antibody do not bind to cells), ii) the internalisation is mediated by EGFR2 internalisation from the surface (acid stripped cells show no surface labelling). Further analysis employing immuno-labelling for endosomal markers, e.g. EEA1, showed extensive co-localisation with EEA1. This demonstrates that the majority of the endocytosed spheres are transported to an early endosomal compartment. A small fraction remains in EEA-negative compartments at the periphery of the cell.

Loading of Caveolin Containing Vesicles

Two different methods have been successfully optimised for loading caveolin containing vesicles with therapeutic drugs.

Uptake of Dye During Caveolin Containing Vesicles Formation by E. coli

Experiments loading fluorescent dyes and chemotherapeutic drug (fluorouracil) showed that agents from the external medium can be incorporated into the caveolin containing vesicles as they form from the membrane. This opens the possibility to introduce peptides and small proteins into caveolin containing vesicles for therapeutic delivery and vaccine development.

E. coli cells harboring expression plasmids for caveolins (as described above) were grown to mid logarithmic growth phase, at least two cell divisions prior to induction of the caveolin protein, fluorescent dyes were added directly to the growth medium. Expression of the caveolin proteins was performed as described above. After induction of the caveolin proteins, the cells were washed extensively with buffered saline to remove residual non-incorporated dye, including dye in the periplasmic space. FIG. 3 shows a model of how small molecules are thought to be internalized into caveolin containing vesicles. Control cells expressing merely the affinity tag, do not incorporate significant amounts of fluorescent dyes as shown in FIGS. 3 and 4. Small molecules that have been successfully incorporated include: 5-(6-)carboxyfluorescein, tetrabromofluorescein, 5-(Dimethylamino)naphthalene-1-sulfonic acid, 5-fluoro-uracil. Furthermore, fluorescent dyes with affinity for E. coli lipids (e.g. 10-nonylacridine orange bromide, 10-NAO) can be incorporated into caveolin containing vesicles as they pinch off the cytoplasmic membrane. Analysis of the affinity purified fluorescent caveolin containing vesicles by sedimentation (100 000 g for 1 hour), shows that caveolin containing vesicles produced by this procedure are extremely stable and largely non-leaky even after extended storage at four degrees Celsius in buffered saline solvents.

Uptake of Drug Using Remote Loading

Loading caveolin containing vesicles with ammonium phosphate during caveolin containing vesicle formation in E. coli and subsequent loading with the chemotherapeutic drug (doxorubicin) was successfully performed. These experiments showed that a number of methods, including the adaptation of methods optimised for (immuno-)liposomes (31), can be used to introduce a drug into caveolin containing vesicles in vitro. This emphasizes the general utility of the method for drug delivery.

Remote Loading of Caveolin Containing Vesicles and Cytotoxicity of Drug-Loaded Caveolin Containing Vesicles Towards Cancer Cells Caveolin containing vesicles engineered with anti-HER2 single chain antibody were produced from cells growing in 300 mM di-basic ammonium phosphate. Following purification by the standard procedure, these caveolin containing vesicles could be very efficiently loaded with doxorubicin in 140 mM sodium chloride and 10 mM HEPES pH 7.4 over night at 8 degrees Celsius, following the method developed by Fritze et al. (31). Free doxorubicin was then removed by extensive ultrafiltration. This demonstrates, that methods optimised for (immuno-)liposomes or other vesicles can be directly adapted to the caveolin containing vesicle system. Human mammary adenocarcinoma cells (SK-BR-3) grown in DMEM (supplemented with 20% fetal bovine serum, 1% L-glutamine) were then incubated with various concentrations of the doxorubicin loaded caveolin containing vesicles as indicated in FIG. 10. The cytotoxic effects were then assayed by means of MTT proliferation assay. A clear dose dependency of the cytotoxicity was observed. Non-loaded caveolin containing vesicles did not have an effect on the proliferation of SK-BR-3. At the highest concentration (22.8 µg/ml growth medium), virtually all cells were dead within 48 hours. Strong doxorubicin fluorescence was readily seen in the nuclei of the cells in some cases already after three hours incubation.

Accumulation of Targeted Caveolin Containing Vesicles at Tumour Site In Vivo

To document usefulness of the caveolin containing vesicles as a drug delivery system, the in vivo accumulation at an orthotopic tumour site was studied. Caveolin containing vesicles with engineered Z-domain (synthetic IgG-binding domain of Protein A) were covalently labelled with carboxyfluorescein. Following amine-conjugation, the caveolin containing vesicles were dialysed extensively and subsequently washed and concentrated by ultrafiltration. The fluorescent caveolin containing vesicles were then allowed to complex with Trastuzumab in saline (0.9% w/v sodium chloride).

The localisation of fluorescence-tagged caveolin containing vesicles was tested in BT474 (HER2+) tumour-bearing female C. B-17-Igh-1b-Prkdc Severe Combined Immunodeficient (SCID) mice. Twelve female SCID mice, which successfully developed tumours from subcutaneously inoculated BT474 (human mammary carcinoma, HER2 overexpressing) cells, were selected for the study. The mice were implanted with a uniquely identified microchip and randomised into three treatment groups of 3 mice each, based on tumour size on Day 0 of the study. The tumour volume range on day 0 was 33.7-122.5 mm3.

Mice were allocated to one of four groups. Group 1; 3 hour collection time-point, Group 2; 12 hour collection time-point, Group 3; 24 hour collection time-point, Group 4; 48 hour collection time-point.

All mice received one dose administration (only) of fluorescein-labelled caveolin containing vesicles by intravenous (i.v.) tail vein injection. At each time-point tumours, liver, kidney, lung, heart and spleen were collected and snap frozen in OCT for subsequent frozen sectioning.

Obvious fluorescence was detected in the tumours 48 hours post-caveolin containing vesicles injection as shown in FIG. 9. The results of organ imaging are summarised in Table 4. Fluorescence was also detected in all organs over the course of the evaluation, which is consistent with the caveolin containing vesicle migration through the body's vasculature.

Stability of Caveolin Containing Vesicles

The long-term stability of caveolin containing vesicles has been assayed for extended storage at four degrees Celsius in saline solutions. The structural integrity of the caveolin containing vesicles was found not to be affected for the duration of more than one year. Furthermore, caveolin containing vesicles were found to be non-leaky with regard to encapsulated, membrane-impermeable molecules. Caveolin containing vesicles were found to be entirely stable in saline, fetal calf serum or horse serum for the duration of the assay (120 hours) upon incubation at thirty-seven degrees Celsius. Both the vesicular nature and the size distribution of the caveolin containing species were not affected by this incubation.

Other Applications

Caveolin containing vesicles have many other potential uses, both in cultured cells and in viva Caveolin containing vesicles can incorporate membrane impermeant agents included in the culture medium (the outer bacterial membrane showing high permeability as compared to the cytoplasmic membrane) as they form from the cytoplasmic membrane of the bacterial host. The unique pathway by which caveolin induces caveolin containing vesicle formation at the cytoplasmic membrane of the bacterium can potentially incorporate co-expressed proteins which are targeted to the periplasmic space. The ability to introduce drugs into caveolin containing vesicles as they form offers tremendous possibilities for generating a targetable genetically-encoded vesicle. The ability to express proteins within the caveolin containing vesicles during formation has potential for vaccine development, in which antigens can be delivered in a vesicle-encapsulated form to generate a specific immune response, and for the delivery of peptide and protein therapeutics in vivo (30).

The simplicity of the system is a huge advantage over alternative vesicle systems as there is considerable pressure to reduce the cost of therapeutics (20). Prokaryotes such as, *E. coli*, are easily grown in high quantities in industrial fermenters. If conditions can be optimised to introduce into *E. coli* caveolin fused to a targeting sequence, such as an ErbB2 binding domain, together with a lumenally-directed therapeutic agent or antigen caveolin containing vesicles could represent a cost-efficient strategy for targeted delivery of drugs or polypeptides or vaccine development.

Membrane proteins are notoriously difficult to express to high levels and purify in *E. coli*. The caveolin containing vesicles system allows co-expression of membrane proteins with caveolin to cause their incorporation into budded caveolin containing vesicles, rather than the cytoplasmic membrane. This reduces toxicity of the membrane proteins (for example channels which would permeabilise the cytoplasmic membrane) to allow their increased expression with perturbing *E. coli* growth or viability. It would also allow their simple one-step purification. The vesicles containing the membrane proteins of interest could be used for structural studies or for functional studies (the membrane proteins being incorporated into a vesicle in a defined orientation, without purification, in contrast to liposome-based reconstitution techniques). The generation of small vesicles containing a membrane protein of therapeutic importance would also have possible therapeutic applications, e.g. delivery of cystic fibrosis transmembrane conductance regulator (CFTR). Additional applications for caveolin containing vesicles include:

1. Caveolin containing vesicles have the potential to allow the expression and delivery of proteins from co-expressed cDNAs without the need for purification of those proteins. This would be an incredibly useful technique for biologists needing to introduce proteins into cells.

2. Incorporation of proteins into caveolin containing vesicles without purification of those proteins offers a cost-effective and efficient way to generate a vesicle encapsulating a protein for therapeutic applications or for vaccine delivery.

3. Incorporation of membrane proteins into caveolin containing vesicles allowing their efficient expression and simple purification, structural or functional characterisation, and therapeutic delivery.

The severe toxicity associated with systemic administration of cytotoxic drugs is a serious problem in medicine today. Targeted drug delivery systems, in which cytotoxic drugs are encapsulated in a vehicle which can target the drug to specific sites in vivo, can avoid the severe toxicity associated with systemic administration of chemotherapeutics. Current strategies to allow targeted drug delivery include liposomes, polymer-based therapeutics, and 'minicells', anucleate particles which can incorporate drugs non-specifically. There is an urgent need for a vesicle-based targeted delivery system which could avoid many of the drawbacks of these strategies. In addition, delivery systems which could efficiently package and deliver protein and peptide therapeutics in a safe and effective form. With many proteins and peptide biotherapeutics already approved for use and already generating billions of dollars in revenue (30), such a delivery system would be of immense value. Herein, it has been established that caveolin containing vesicles have a number of properties which suggest their utility for in vivo therapeutic applications (Table 3). For example, caveolin containing vesicles contain no detectable bacterial proteins, they can incorporate exogenous agents into their lumen, they are extremely small and uniform, and they can be readily endocytosed by mammalian cells.

An interesting comparison can be made with bacterial minicells (or nanocells) and anucleate bacterial cells (16-19). Minicells are 10-fold larger in diameter reducing their penetration into tissues, and uptake by endocytosis. Minicells can be phagocytosed but cannot be taken up by conventional forms of endocytosis in cells such as Cos7 and HeLa (17). In contrast, it has been shown have shown that caveolin containing vesicles are readily endocytosed by mammalian cells. Minicells incorporate bioactive molecules through passive non-selective mechanisms (19). In contrast caveolin containing vesicles can incorporate membrane impermeant agents included in the culture medium (the outer bacterial membrane showing high permeability as compared to the cytoplasmic membrane) as they form from the cytoplasmic membrane of the bacterial host. The unique pathway by which caveolin induces caveolin containing vesicle formation at the cytoplasmic membrane of the bacterium can potentially incorporate co-expressed proteins which are targeted to the periplasmic space. The ability to introduce drugs into caveolin containing vesicles as they form offers tremendous possibilities for generating a targetable genetically encoded vesicle. The ability to express proteins within the caveolin containing vesicles during formation could have potential for vaccine development, in which antigens can be delivered in a vesicle-encapsulated form to generate a specific immune response, and for the delivery of peptide and protein therapeutics in vivo (30).

Advantages of the caveolin containing vesicles include that they are uniform nanovesicles, 45-55 nm in diameter, requiring at least the expression of one caveolin protein and no detectable bacterial proteins. These features are all advantageous ones when compared to conventional technologies such as mini-cells.

The caveolin containing vesicles are made by an extremely simple one-step expression and one-step purification systems. This simple process allows purification to a high concentration.

A linking protein can be attached to caveolin to allow targeting to specific sites, for example, protein A may be added to bind antibodies to target caveolin containing vesicles to ErbB2 over-expressing tumours. As reported herein, caveolin containing vesicles comprised of protein A-caveolin fusion protein show Herceptin-dependent uptake into ErbB2-positive cells.

The caveolin containing vesicles are extremely small compared to other delivery agents. The caveolin containing vesicles are an order of magnitude smaller than 'minicells', which allows them to be taken up by endocytosis, not phagocytosis and should allow for improved penetration through tissues.

There is potential for incorporation of drugs into the caveolin containing vesicles as they form. Herein it has been shown that fluorescent markers efficiently incorporate into caveolin containing vesicles. Remote loading of doxorubicin and in vivo loading with 5-fluorouracil has also been shown.

The caveolin containing vesicles have potential for incorporation of proteins for delivery to cells uniquely by co-expression in *E. coli*. Accordingly, no purification of the protein to be incorporated is required.

The caveolin containing vesicle of the invention has the significant advantage of relatively small size which leads to efficient endocytosis and delivery to a site of interest. Additionally, the caveolin containing vesicle of the invention can be purified in high quantities and is highly stable.

The caveolin containing vesicle has numerous applications, ranging from drug delivery in vivo to protein transfer into mammalian cells without the need for protein purification.

The targeted delivery of molecules such as drugs accomplished by the present invention may reduce side-effects of drug therapy.

The caveolin containing vesicle of the invention can be easily produced, does not leak and production can be easily scaled up.

The invention allows production of small, uniformly-sized vesicles to be generated by expression of a vertebrate (preferably mammalian) protein in a prokaryotic host. These vesicles, which contain no detectable bacterial proteins, bud in from the cytoplasmic membrane until the host is filled by these vesicles.

These vesicles can be isolated to high purity in a single step.

Importantly, foreign agents can be incorporated into the vesicles in an extremely specific manner as they pinch from the membrane.

Of equal importance and significance is the finding that the protein which induces, and coats, the exterior of the nanovesicles, can be engineered to target the nanovesicles to specific cell types or even to provide the vesicles with fusogenic properties.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

Tables

TABLE 1

Expression systems in place for the expression of caveolin containing vesicles in various, biotechnologically relevant prokaryotic systems.

|  | Promoter for expression/expression system | Cloned |
|---|---|---|
| Gram⁻ eubacteria | | |
| *Escherichia coli* (standard system) | T7 RNA pol./β-galactoside (lacUV5), ara BAD (*E. coli* RNA pol.), arabinose | ✓ |
| *Pseudomonas aeruginosa* | T7 RNA pol., β-galactoside | ✓ |
| Gram+ eubacteria | | |
| *Bacillus subtilis* | $P_{spac}$ β-galactoside and $P_{xylA}$, xylose | ✓ |
| *Lactococcus lactis* | $P_{nisA}$, Nisin (NICE system) | ✓ |
| *Streptomyces lividans/ S. coelicolor* | $P_{nitA}$ (Nitrilase), ε-caprolactam | ✓ |
| *Coryneybacterium glutamicum* | $P_{trac}$, β-galactoside | ✓ |
| Archaea | | |
| *Haloferax volcanii* | $P_{tna}$ (tryptophanase), tryptophan | ✓ |

TABLE 2

Phospholipid (PL) composition of total extractable lipids in whole membranes and purified caveolin containing vesicles.

| PL species | Frequency* in: | | | | |
|---|---|---|---|---|---|
| Sum acyl composition | $t_0$ control cells | control cells | $t_0$ cav cells | cav cells | CCVs‡ |
| PA C32:1 | 1 | 0.73 | 0.70 | 0.43 | 0.37 |
| PE C32:0 | 1 | 1 | 0.88 | 0.58 | 0.67 |
| PE C33$^{cyc}$ | 1 | 1.12 | 0.91 | 0.84 | 0.76 |
| PE C34:1 | 1 | 1.03 | 1.13 | 1.57 | 1.45 |
| PE C36:2 | 1 | 1.15 | 1.23 | 1.79 | 2.08 |
| PG C34:1 | 1 | 0.75 | 1.30 | 1.66 | 2.27 |
| PG C36:2 | 1 | 0.65 | 1.30 | 1.63 | 2.08 |

$t_0$ represents non-induced, whole cell extraction.
CCVs are affinity purified caveolin containing vesicles.
"control cells" and "cav cells" are whole cell lipid extracts from MBP-expressing and MBP-caveolin1-expressing cells, respectively.
PA, phosphatidic acid;
PE, phosphatidylethanolamine;
PG, phosphatidylglycerol
*relative abundancy normalised to relative abundancy in uninduced control cells (expressing fusion partner (MBP) only)
‡affinity purified caveolin containing vesicles/CCVs
$^{cyc}$cyclopropanation of cis-unsaturated fatty acids by addition of methylene group

TABLE 3

Properties of caveolin containing vesicles

Uniform nanovesicles, 45-55 nm in diameter, expressing single mammalian protein and no detectable bacterial proteins (cf. bacterial 'minicells').
Extremely simple one-step expression and one-step purification systems; purification to high concentration.
A linking protein can be attached to caveolin to allow targeting to specific sites, eg. protein A to bind antibody to target caveolin containing vesicles to ErbB2 over-expressing tumours.
Proof of principle: caveolin containing vesicles comprised of protein A-caveolin fusion protein show herceptin-dependent uptake into ErbB2-positive cells.
Extremely small compared to other delivery agents (order of magnitude smaller than 'minicells') allowing uptake by endocytosis, not phagocytosis, and excellent penetration through tissues.
Potential for incorporation of drugs into caveolin containing vesicles as they form.
Proof of principle: fluorescent markers efficiently incorporated into caveolin containing vesicles, remote loading of doxorubicin, in vivo loading with 5-fluorouracil.
Potential for incorporation of proteins into caveolin containing vesicles for delivery to cells simply by co-expression in *E. coli* - no purification of the protein to be incorporated is required.

TABLE 4

Detection of fluorescein-labeled caveolin containing vesicles in organs of BT474 implanted nude mice.
The fluorescence in various organs and tumours was assessed by fluorescence microscopy of the excised organs/tumours.

| Group | ID | T-p | T | Lu | Li | H | S | K |
|---|---|---|---|---|---|---|---|---|
| 1 | 246984 | 3 | − | + | − | − | − | + |
|  | 246088 |  | − | + | − | + | + | − |
|  | 247332 |  | − | + | − | − | − | + |
| 2 | 248526 | 12 | w+ | w+ | − | − | − | − |
|  | 245717 |  |  | w+ | + | − | + | − | +  |
|  | 248893 |  | w+ | + | − | − | − | w+ |
| 3 | 245375 | 24 | + | − | − | − | − | − |
|  | 247858 |  | + | − | − | − | − | − |
|  | 246348 |  | + | − | w+ | − | − | − |

TABLE 4-continued

Detection of fluorescein-labeled caveolin containing vesicles in organs of BT474 implanted nude mice. The fluorescence in various organs and tumours was assessed by fluorescence microscopy of the excised organs/tumours.

| Group | ID | T-p | T | Lu | Li | H | S | K |
|-------|--------|-----|---|----|----|---|----|---|
| 4 | 247112 | 48 | + | − | − | − | w+ | + |
|   | 247103 |    | + | − | − | − | −  | + |
|   | 247936 |    | + | − | − | − | w+ | − |

Key:
ID = Animal ID number;
w = weak;
T-p = time-point (h);
T = tumour;
L = Lu = lung;
Li = liver;
H = heart;
S = spleen; and
K = kidney.

REFERENCES

1. Yu, J., Bergaya, S., et al. (2006) J Clin Invest 116, 1284-1291.
2. Sedding, D. G., Hermsen, J., et al. (2005) Circ Res 96, 635-642.
3. Razani, B., Combs, T. P., et al. (2002) J. Biol. Chem. 277, 8635-8647.
4. Williams, T. M., and Lisanti, M. P. (2005) Am J Physiol Cell Physiol 288, C494-506.
5. Li, T., Sotgia, F., et al. (2006) Am J Pathol 168, 1998-2013.
6. Sunaga, N., Miyajima, K., et al. (2004) Cancer Res 64, 4277-4285.
7. Yang, G., Timme, T. L., et al. (2005) Cancer 103, 1186-1194.
8. McNally, E. M., de Sa Moreira, E., et al. (1998) Hum Mol Genet 7, 871-877.
9. Minetti, C., Sotgia, F., et al. (1998) Nat Genet 18, 365-368.
10. Rothberg, K. G., Heuser, J. E., et al. (1992) Cell 68, 673-682.
11. Tahir, S. A., Yang, G., Ebara, S., et al. (2001) Cancer Res 61, 3882-3885.
12. Eaton, L. C., Erdos, G. W., Vreeland, N. L., et al. (1981) J Bacteriol 146, 1151-1153.
13. Takamori, S., Holt, M., et al. (2006) Cell 127, 831-846.
14. Thiele, C., Hannah, M. J., Fahrenholz, F., et al. (2000) Nat Cell Biol 2, 42-49
15. Pelkmans, L., Burli, T., Zerial, M., et al. (2004) Cell 118, 767-780.
16. Giacalone, M. J., Gentile, A. M., et al. (2006) Cellular microbiology 8, 1624-1633.
17. Giacalone, M. J., Sabbadini, R. A., et al. (2006) Vaccine 24, 6009-6017.
18. MacDiarmid, J. A., Madrid-Weiss, J., et al. (2007) Cell cycle 6, 2099-2105.
19. MacDiarmid, J. A., Mugridge, N. B., Weiss, J. C., et al. (2007) Cancer cell 11, 431-445.
20. Gregson, N., Sparrowhawk, K., et al. (2005) Nature reviews 4, 121-130.
21. Yamaguchi, K., Yu, F., et al. (1988) Cell 53, 423-432.
22. Szeto, T. H., Rowland, S. L., et al. (2003) J. Biol. Chem 278, 40050-40056.
23. Zehnder-Fjallman, A. H., Marty, C., et al. (2007) Oncology reports 18, 933-941.
24. Boldicke, T., Tesar, M., et al. (2001) Stem cells 19, 24-36.
25. Graff, C. P., Chester, K., et al. (2004) Protein Eng Des Sel 17, 293-304.
26. Han, X., Bushweller, J. H., et al. (2001) Nature structural biology 8, 715-720.
27. Hayward, R. D., McGhie, E. J., et al. (2000) Molecular microbiology 37, 727-739.
28. Stacey, K. J., Young, G. R., et al. (2003) J Immunol 170, 3614-3620.
29. Liu, W. J., Liu, X. S., et al. (2000) Virology 273, 374-382.
30. Kumar T. R., et al. (2006) Curr Pharm Biotechnol. 7, 261-276.
31. Fritze A., et al. (2006). Biochim et Biophys Acta 1758, 1633-1640.

The invention claimed is:

1. An isolated caveolin containing vesicle comprising a caveolin protein and at least one lipid, wherein at least about 30% of the at least one lipid is selected from phosphatidylethanolamine and phosphatidylglycerol.

2. The isolated caveolin containing vesicle of claim 1 wherein the caveolin protein is a prokaryotically expressed recombinant caveolin protein.

3. The isolated caveolin containing vesicle of claim 1 wherein at least about 50% of the at least one lipid is selected from phosphatidylethanolamine and phosphatidylglycerol.

4. The isolated caveolin containing vesicle of claim 2 wherein at least a portion of the at least one lipid is endogenous to, or produced by, a prokaryote in which the prokaryotically expressed recombinant caveolin protein was expressed.

5. The isolated caveolin containing vesicle of claim 1 wherein the vesicle also comprises cardiolipin.

6. The isolated caveolin containing vesicle of claim 1 wherein the caveolin protein is a bacterially expressed recombinant caveolin protein.

7. The isolated caveolin containing vesicle of claim 1 further comprising a targeting molecule.

8. A method of making an isolated caveolin containing vesicle including the step of allowing a caveolin protein to associate with at least one lipid, wherein at least about 30% of the at least one lipid is selected from phosphatidylethanolamine and phosphatidylglycerol, to thereby make the isolated caveolin containing vesicle.

9. The method of claim 8 wherein the caveolin protein is a prokaryotically expressed recombinant caveolin protein.

10. The method of claim 8 wherein at least about 50% of the at least one lipid is selected from phosphatidylethanolamine and phosphatidylglycerol.

11. The method of claim 9 wherein at least a portion of the at least one lipid is endogenous to or produced by a prokaryote in which the prokaryotically expressed recombinant caveolin protein was expressed.

12. The method of claim 8 wherein the vesicle also comprises cardiolipin.

13. The method of claim 8 wherein the caveolin protein is a bacterially expressed recombinant caveolin protein.

14. An isolated caveolin containing vesicle comprising a recombinant caveolin protein expressed in a prokaryote associated with at least one lipid; wherein the recombinant caveolin protein and the at least one lipid associate in the prokaryote.

15. The isolated caveolin containing vesicle of claim 14 wherein at least about 30% of the at least one lipid is selected from phosphatidylethanolamine and phosphatidylglycerol.

16. The isolated caveolin containing vesicle of claim 14 wherein at least about 50% of the at least one lipid is selected from phosphatidylethanolamine and phosphatidylglycerol.

17. The isolated caveolin containing vesicle of claim 14 wherein at least a portion of the at least one lipid is endogenous to, or produced by, the prokaryote.

18. The isolated caveolin containing vesicle of claim 14 wherein the isolated caveolin containing vesicle also comprises cardiolipin.

19. The isolated caveolin containing vesicle of claim 14 wherein the prokaryote is a bacteria.

20. The isolated caveolin containing vesicle of claim 14 wherein the isolated caveolin containing vesicle further comprises a targeting molecule.

21. A method of making an isolated caveolin containing vesicle including the steps of: expressing a recombinant caveolin protein in a prokaryote; and allowing the expressed recombinant caveolin protein to associate with at least one lipid in the prokaryote; to thereby make the isolated caveolin containing vesicle.

22. The method of claim 21 wherein at least about 30% of the at least one lipid is selected from phosphatidylethanolamine and phosphatidylglycerol.

23. The method of claim 21 wherein at least about 50% of the at least one lipid is selected from phosphatidylethanolamine and phosphatidylglycerol.

24. The method of claim 21 wherein at least a portion of the at least one lipid is endogenous to, or produced by, the prokaryote.

25. The method of claim 21 wherein the isolated caveolin containing vesicle also comprises cardiolipin.

26. The method of claim 21 wherein the prokaryote is a bacteria.

27. The method of claim 21 wherein the method further comprises expressing a targeting molecule in the prokaryote and allowing the targeting molecule to associate with the expressed recombinant caveolin and the at least one lipid in the prokaryote.

28. An isolated caveolin containing delivery vesicle comprising: a caveolin protein; at least one lipid; wherein at least about 30% of the at least one lipid is selected from phosphatidylethanolamine and phosphatidylglycerol; and a molecule to be delivered by the vesicle.

29. The isolated caveolin containing delivery vesicle of claim 28 wherein the molecule to be delivered by the vesicle is contained within the vesicle.

30. The isolated caveolin containing delivery vesicle of claim 28 wherein the molecule to be delivered by the vesicle is integrated into a vesicle membrane.

31. The isolated caveolin containing delivery vesicle of claim 28 wherein the molecule to be delivered by the vesicle is peripherally associated with a vesicle membrane.

32. A method of making an isolated caveolin containing delivery vesicle, the method including the step of allowing a caveolin protein to associate with at least one lipid and a molecule to be delivered by the vesicle, wherein at least about 30% of the at least one lipid is selected from phosphatidylethanolamine and phosphatidylglycerol, to thereby make the isolated caveolin containing delivery vesicle.

33. The method of claim 32 wherein the caveolin protein and a molecule to be delivered are co-expressed in a prokaryote.

34. The method of claim 32 wherein a prokaryote expressing the caveolin protein is exposed to the molecule to be delivered.

35. The method of claim 32 wherein the caveolin protein is prokaryotically expressed and allowed to associate with the at least one lipid to form an isolated caveolin containing vesicle and the isolated caveolin containing vesicle is allowed to associate with the molecule to be delivered by the vesicle.

36. A method of making an isolated caveolin containing delivery vesicle, the method including the steps of: co-expressing a caveolin protein and a molecule to be delivered; and allowing the caveolin protein to associate with at least one lipid and the molecule to be delivered by the vesicle; to thereby make the isolated caveolin containing delivery vesicle.

37. The method of claim 36 wherein at least about 30% of the at least one lipid is selected from phosphatidylethanolamine and phosphatidylglycerol.

38. The method of claim 36 wherein the caveolin protein and the molecule to be delivered are co-expressed in a prokaryote.

39. A method of treatment of a disease or condition by delivery of a molecule using the isolated caveolin containing delivery vesicle of claim 28 to thereby treat said disease or condition.

40. The method of claim 39 wherein the molecule to be delivered has therapeutic activity.

41. A method of treatment of a disease or condition by delivery of a molecule using an isolated caveolin containing delivery vesicle made according to claim 32 to thereby treat said disease or condition.

42. The method of claim 41 wherein the molecule to be delivered has therapeutic activity.

43. A method for delivery of a molecule using the isolated caveolin containing delivery vesicle of claim 28 to thereby deliver said molecule.

44. A method for delivery of a molecule using an isolated caveolin containing delivery vesicle made according to claim 32 to thereby deliver said molecule.

45. A composition comprising the isolated caveolin containing delivery vesicle of claim 28 and a pharmaceutically acceptable carrier, diluent or excipient.

46. A composition comprising an isolated caveolin containing delivery vesicle and a pharmaceutically acceptable carrier, diluent or excipient,
wherein the isolated caveolin containing delivery vesicle is made by a method comprising allowing the caveolin protein to associate with at least one lipid and the molecule to be delivered by the vesicle, wherein at least about 30% of the at least one lipid is a phosphatidylethanolamine, a phosphatidylglycerol or a combination thereof.

* * * * *